US012582292B2

(12) United States Patent
Lewitzky et al.

(10) Patent No.: US 12,582,292 B2
(45) Date of Patent: Mar. 24, 2026

(54) GRASPING CAP FOR OVER-THE-SCOPE APPLICATIONS

(71) Applicant: BOSTON SCIENTIFIC SCIMED, INC., Maple Grove, MN (US)

(72) Inventors: Jennifer Lewitzky, Lexington, MA (US); Colby Harris, Norfolk, MA (US); Allison Kumarasena, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 233 days.

(21) Appl. No.: 18/588,569

(22) Filed: Feb. 27, 2024

(65) Prior Publication Data

US 2024/0358230 A1     Oct. 31, 2024

Related U.S. Application Data

(60) Provisional application No. 63/498,396, filed on Apr. 26, 2023.

(51) Int. Cl.
*A61B 1/00* (2006.01)

(52) U.S. Cl.
CPC ...... *A61B 1/00087* (2013.01); *A61B 1/00135* (2013.01)

(58) Field of Classification Search
CPC ............ A61B 1/00087; A61B 1/00135; A61B 17/22031; A61B 2017/00269; A61B 17/083; A61B 17/10; A61B 2017/00296; A61B 1/00101; A61B 2017/00818; A61B 2017/306; A61B 1/0052; A61B 1/0057; A61B 1/31; A61B 1/2736
See application file for complete search history.

(56) References Cited

U.S. PATENT DOCUMENTS

| 2014/0228875 A1 | 8/2014 | Saadat |
| 2017/0119234 A1 | 5/2017 | Petroskey |
| 2022/0378432 A1* | 12/2022 | Sharma .............. A61B 1/00135 |
| 2023/0054185 A1* | 2/2023 | Singh ................... A61B 17/083 |

FOREIGN PATENT DOCUMENTS

| EP | 2 868 280 A1 | 5/2015 |
| JP | H10137251 A | 5/1998 |

* cited by examiner

*Primary Examiner* — Amit Chatly
(74) *Attorney, Agent, or Firm* — Fay Kaplun & Marcin, LLP

(57) ABSTRACT

A device is for facilitating an over-the-scope application of a tissue treating element and includes an end cap and control members. The cap includes a proximal portion mounted over a distal end of a scope device and a distal portion including flaps. The proximal portion extends along a longitudinal axis from a proximal end to a distal end and includes a proximal channel extending therethrough. A proximal end of each flap is pivotally connected to the distal end of the proximal portion so that the flaps are movable between a closed configuration and an expanded configuration. A distal end of each of the members is connected to a corresponding flap so that a longitudinal movement of the members relative to the proximal portion of the cap moves the flaps relative to the proximal portion between the closed and expanded configurations.

19 Claims, 6 Drawing Sheets

GRASPING CAP FOR OVER-THE-SCOPE APPLICATIONS

PRIORITY CLAIM

The present disclosure claims priority to U.S. Provisional Patent Application Ser. No. 63/498,396 filed Apr. 26, 2023; the disclosure of which is incorporated herewith by reference.

FIELD

The present disclosure relates to endoscopic devices and, in particular, relates to an end cap for over-the-scope applications for treating tissue along the gastrointestinal tract.

BACKGROUND

Physicians have become more willing to perform aggressive interventional and therapeutic endoscopic gastrointestinal (GI) procedures, which may increase the risk of perforating the wall of the GI tract or which may require closure of one or more openings through the wall of the GI tract wall as part of the procedure. Such procedures may include, for example, the removal of large lesions, tunneling under the mucosal layer of the GI tract to treat issues below the mucosa, full thickness removal of tissue, treatment of organs outside the GI tract by inserting a device through the GI tract to a location adjacent to the organ to be treated and passing the device through the wall of the GI tract to reach the target organ. Endoscopic treatment/repair of post-surgical issues (e.g., post-surgical leaks, breakdown of surgical staple lines, anastomotic leaks or for the closure of any surgically created openings in the wall of the GI track) may then be required.

Currently, tissue may be treated via endoscopic closure devices including through-the scope clips and/or over-the-scope clips. Over-the-scope clips (OTSCs) may be particularly useful for achieving closure of larger tissue defects. A typical OTSC may be placed over a plastic applicator cap mounted on a distal end of an endoscope (e.g., gastroscope, a colonoscope, etc.). The OTSC remains on the cap as the scope is navigated through the GI track until the clip is positioned as desired and released from the scope to clip the target tissue. These applicator caps are often translucent to permit some visibility therethrough and hollow to permit suction of target tissue therein. Tissue is drawn into the cap via, e.g., suction, for an extent sufficient so that when the user releases the clip from the cap, it will close over sufficient layers of the GI tract to ensure secure closure of a tissue opening.

Some current cap designs, however, may hinder long-term success. In some cases, depending on the surface area of a tissue defect to be treated, the cap's depth and interior diameter may limit the amount of tissue that may suctioned, thereby preventing the clip from achieving a sufficient and/or full-thickness clipping of the tissue. Additionally, in some cases, the amount of tissue accessible to the clip may be limited by the scope's suction force or by the force that may be applied to tissue by any other mechanism for drawing tissue into the cap (e.g., graspers). This may be more likely in the case of, for example, chronic or fibrotic tissue, which may result in superficial placement or low bite quality of the clip. Further, since the cap extends from the distal tip of the scope, it may limit the clinician's field of view of the GI tract. Although such caps are generally translucent, they are generally not clear enough to permit unimpeded vision therethrough and they may block a user's peripheral field of vision and limit the visibility range to the interior diameter of the cap.

SUMMARY

The present disclosure relates to a device for facilitating an over-the-scope application of a tissue treating element. The device includes an end cap and a plurality of control members. The end cap includes a proximal portion configured to be mounted over a distal end of a scope device and a distal portion extending distally therefrom. The proximal portion extends along a longitudinal axis from a proximal end to a distal end and includes a proximal channel extending therethrough. The distal portion includes a plurality of flaps. A proximal end of each of the flaps is pivotally connected to the distal end of the proximal portion so that the flaps are movable between a closed configuration, in which the flaps define a distal channel in alignment with the proximal channel, and an expanded configuration, in which distal ends of the flaps are moved away from one another to expand a distal opening of the end cap. A distal end of each of the control members is connected to a corresponding one of the flaps so that a longitudinal movement of the control members relative to the proximal portion of the end cap moves the flaps relative to the proximal portion between the closed configuration and the expanded configuration.

In an embodiment, an interior surface of the plurality of flaps includes a plurality of gripping features configured to anchor the flaps to s target tissue.

In an embodiment, the plurality of gripping features includes teeth protruding from the interior surface of the plurality of flaps.

In an embodiment, an exterior surface of each of the plurality of flaps are curved to facilitate a sliding of a tissue clipping device therealong.

In an embodiment, in the closed configuration, each of the flaps extend substantially parallel relative to the longitudinal axis and a longitudinal edge of each of the flaps contacts a longitudinal edge of an adjacent one of the flaps to define the distal channel therebetween.

In an embodiment, the distal end of each of the control members are connected to an exterior surface of the corresponding one of the flaps so that the control members extend along an exterior of the end cap.

In an embodiment, the distal end of each of the control members are connected to an interior surface of each of the corresponding one of the flaps so that the control members extend proximally therefrom through the proximal channel of the end cap.

In an embodiment, the distal end of each of the control members includes an enlarged ball received within a correspondingly shaped socket of a yoke component that is connected to the corresponding one of the plurality of flaps, the ball rotatable within the socket as the end cap is moved between the closed configuration and the expanded configuration.

In an embodiment, each of the plurality of flaps includes a longitudinal groove extending therealong and the proximal portion includes a corresponding groove therealong in longitudinal alignment with the longitudinal groove, the longitudinal groove and the corresponding groove configured to receive the control member therein.

In an embodiment, the end cap further includes a flexible membrane extending between adjacent ones of the plurality of flaps so that, in the expanded configuration, the flexible membrane stretches to increase a cross-sectional area of the distal channel.

In an embodiment, the flexible membrane is formed of a material including one of silicone and PET thermoplastic.

The present disclosure also relates to an end cap which is configured to be mounted over a distal end of a scope to facilitate to facilitate an over-the-scope application of a tissue gripping device. The end cap includes a proximal portion extending along a longitudinal axis from a proximal end to a distal end and includes a proximal channel extending therethrough. The end cap also includes a distal portion which has a plurality of flaps. A proximal end of each of the flaps is pivotally connected to the distal end of the proximal portion so that the flaps are movable between a closed configuration, in which the flaps define a distal channel in alignment with the proximal channel, and an expanded configuration, in which distal ends of the flaps are moved away from one another.

In an embodiment, an interior surface of the plurality of flaps includes a plurality of gripping features configured to anchor the flaps to a target tissue.

In an embodiment, in the closed configuration, each of the flaps extend substantially parallel relative to the longitudinal axis and a longitudinal edge of each of the flaps contacts a longitudinal edge of an adjacent one of the flaps to define the distal channel therebetween.

In an embodiment, the end cap further includes a flexible membrane extending between adjacent ones of the plurality of flaps so that, in the expanded configuration, the flexible membrane stretches to increase a cross-sectional area of the distal channel.

In addition, the present disclosure relates to a method for treating tissue. The method includes mounting an end cap over a distal end of a scope device and inserting the distal end of the scope device, with the end cap in a closed configuration, to a target area within a body lumen to be treated, the end cap including a proximal portion defining a proximal channel therein and a distal portion including a plurality of flaps, a proximal end of each of the flaps pivotally coupled to the proximal portion, the plurality of flaps contacting one another to define a distal channel therebetween, in the closed configuration; moving the end cap from the closed configuration toward an expanded configuration by pivoting the flaps relative to the proximal portion so that distal ends of the flaps are moved away from one another to expand a distal opening of the proximal channel; applying a suction through the end cap to suction a target tissue therein; moving the end cap from the expanded configuration toward the closed configuration to draw the suctioned tissue further into the end cap; and sliding an over-the-scope clip, positioned over the proximal portion of the end cap, distally off of the end cap to be clipped over the target tissue.

In an embodiment, the claim further includes pressing tissue gripping features along an interior surface of the plurality of flaps along the target tissue to anchor the flaps to the target tissue so that moving the end cap from the expanded configuration toward the closed configuration draws the target tissue into the distal channel formed via the plurality of flaps.

In an embodiment, the flaps are moved between the closed configuration and the expanded configuration via a plurality of control members, a distal end of each of the control members connected to a corresponding one of the flaps so that a longitudinal movement of the control members relative to the proximal portion of the end cap and the scope device correspondingly moves the flaps between the closed configuration and the expanded configuration.

In an embodiment, in the closed configuration, each of the flaps extend substantially parallel relative to a longitudinal axis so that the end cap extends along a substantially cylindrical shape.

In an embodiment, the distal end of the control members are connected to the flaps of the end cap via a ball and yoke mechanism.

BRIEF DESCRIPTION

DETAILED DESCRIPTION

Figure 1:
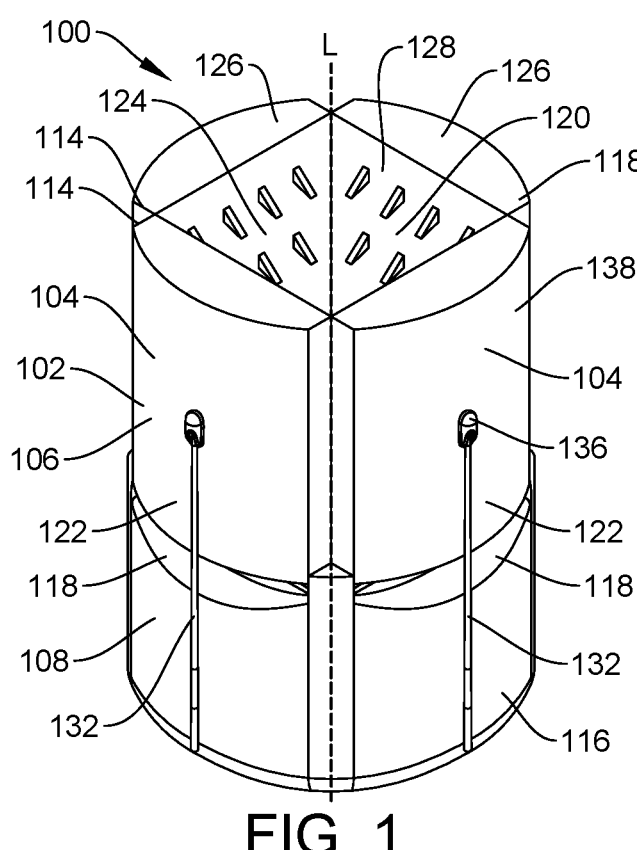
FIG. 1 shows a perspective view of a device according to an exemplary embodiment of the present disclosure, in a closed configuration.

The present disclosure may be further understood with reference to the following description and the appended drawings, wherein like elements are referred to with the same reference numerals. The present disclosure relates to scope systems and, in particular, relates to an end cap for over-the-scope applications such as, for example, over-the-scope clips and bands. Exemplary embodiments of the present disclosure describe an expandable end cap including a plurality of flaps extending along a distal portion thereof and pivotally connected to a proximal portion of the cap so that the flaps are movable between a closed configuration, in which sections of the distal portion of the cap are drawn together to extend distally in a substantially tubular configuration to minimize navigational issues and trauma to tissue past which the scope is advanced. The cap is configured to be moved to an expanded configuration in which distal ends of the flaps are pivoted away from one another, opening a distal end of the cap to allow a larger surface area of tissue to be suctioned into the cap.

In an exemplary embodiment, the flaps may also include gripping features such as, for example, teeth, protruding therefrom to grasp target tissue drawn into the cap to anchor the target tissue within the cap. The gripping features may be particularly useful for defects involving fibrotic or chronic tissue that is resistant to suctioning. With two methods for drawing tissue into the cap—i.e., suction in conjunction with the gripping features along the flaps—a high quality, full-thickness bite of the target tissue via the over-the-scope device (e.g., clip or band) is more likely. The cap, in the expanded configuration, also increases a peripheral field of view of the vision system of the scope (i.e., by moving the flaps out of the field of view of the vision system), leading to increased confidence in clip or band placement.

According to an exemplary embodiment, an over-the-scope clip is placed immediately proximal of the flaps so that, tissue may be drawn into the cap in the expanded configuration and the cap is then moved from the expanded configuration to the closed configuration so that the clip may then be moved distally along the flaps until the clip is moved distally off of the cap and released to be clipped over the target tissue. It will be understood by those of skill in the art that although the exemplary embodiments show and describe an over-the-scope clip, other over-the-scope tissue closure devices such as, for example, bands, may also be used in conjunction with any of the exemplary caps described herein. It should be noted that the terms proximal and distal, as used herein, refer to a direction toward (proximal) and away from (distal), respectively, a user of the device.

As shown in FIGS. 1-9, a device 100 according to an exemplary embodiment of the present disclosure comprises an end cap 102 configured to be mounted over a distal end of a scope device such as, for example, a gastroscope or a colonoscope, to facilitate over-the-scope applications such as placement of an over-the-scope clip or other tissue closure device over target tissue within the GI tract (e.g., to close an opening in a wall of the GI tract). The end cap 102, as shown in FIGS. 1-4, includes a plurality of flaps 104 forming a distal portion 106 of the cap 102. Each of the flaps 104 is pivotally connected to a proximal portion 108 of the cap 102 so that the flaps 104 are movable relative to the proximal portion 108 between a closed configuration (shown in FIGS. 1 and 3), in which the end cap 102 (including both the proximal portion 108 and the distal portion 106) forms a substantially continuous tubular shape, and an expanded configuration (shown in FIGS. 2 and 4), in which the distal ends of the flaps 104 pivot away from one another (about a hinge formed between the flaps 104 and the proximal portion 108 to radially expand the distal portion 106 of the end cap 102 and to remove the flaps 104 from a position in which they may obstruct a portion of the field of view of the vision system of the scope (or to minimize any such field of view obstruction).

In the closed configuration, the end cap 102 is sized and shaped to fit tightly over the distal end of the scope so that the scope may be navigated with minimal interference from the cap 102 through, for example, a body lumen, to a target area to be treated. Once the scope has reached the target area, the cap 102 may be moved from the closed configuration to the expanded configuration as described above. Target tissue may then be drawn into the end cap 102 by applying a suction (or graspers or any other suitable tissue manipulating device) through a working channel of the scope and, as the cap 102 surrounds a distal opening of the working channel, the suction is applied through the cap 102 to draw tissue into the cap 102.

The flaps 104 may then be moved from the expanded configuration back to the closed configuration, so that the tissue may be engaged by the gripping features 112 along an interior surface 130 of the flaps 104 to help retain the tissue within the cap 102 and to draw the tissue further into the end cap 102. One or more over-the-scope clip(s), or other over-the-scope grasping/gripping element(s), positioned around the proximal portion 108 of the end cap 102, may then be moved distally over the flaps 104 to pass distally off of the end cap 102 and clip target tissue. As will be described in further detail below, the end cap 102 may be moved between the open and the closed configurations via a plurality of control members 132.

Figures 5, 6:
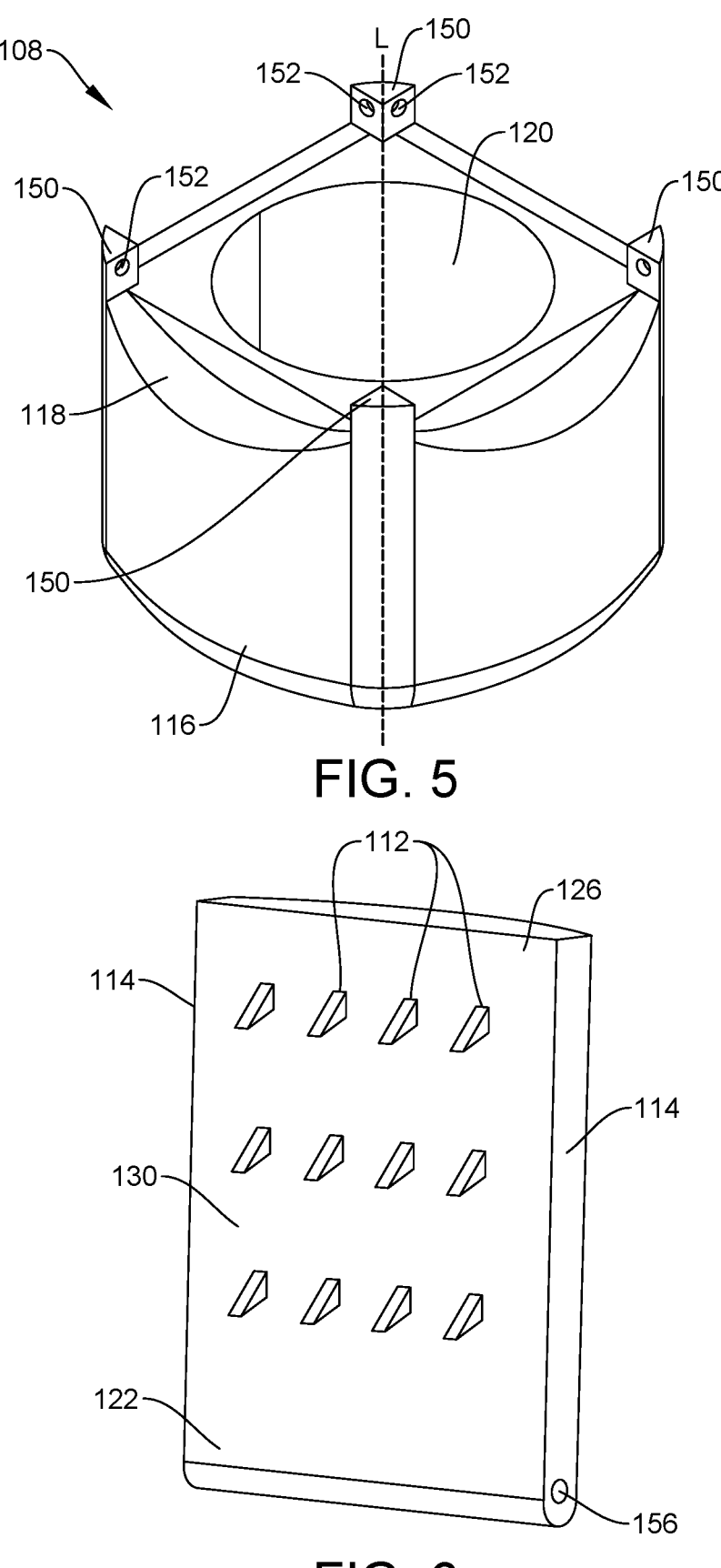
FIG. 5 shows a perspective view of a proximal portion of an end cap according to the device of FIG. 1.
FIG. 6 shows a perspective view of a distal portion of an end cap according to the device of FIG. 1.

As shown in FIG. 5 and as discussed above, the end cap 102 includes the proximal portion 108 and the distal portion 106. The proximal portion 108 extends along a longitudinal axis L from a proximal end 116 to a distal end 118 and defines a channel 120 extending therethrough so that, in an exemplary embodiment, the proximal portion 108 has a tubular configuration generally sized and shaped to accommodate the distal end of a scope over which it is to be mounted. The channel 120 of the proximal portion 108 is sized, shaped, and configured to be mounted over the distal end of the scope device and, as would be understood by those skilled in the art may take any size and shape required to obtain the desired fit over the scope (e.g., a friction fit).

In an exemplary embodiment, the channel 120 of the proximal portion 108 is substantially cylindrical and an outer surface of the cap 102 is sized, shaped, and configured to accommodate the over-the-scope clip, or other over-the-scope grasping/clipping element, to be mounted over an exterior thereof. Those skilled in the art will understand that the channel 120 and the outer surface of the cap 102 are sized and shaped so that, clips, ligation bands, etc. to be mounted over the cap 102 will, when mounted thereon, be stretched open to an extent required to permit the desired amount of tissue to be drawn thereinto.

Figure 2:
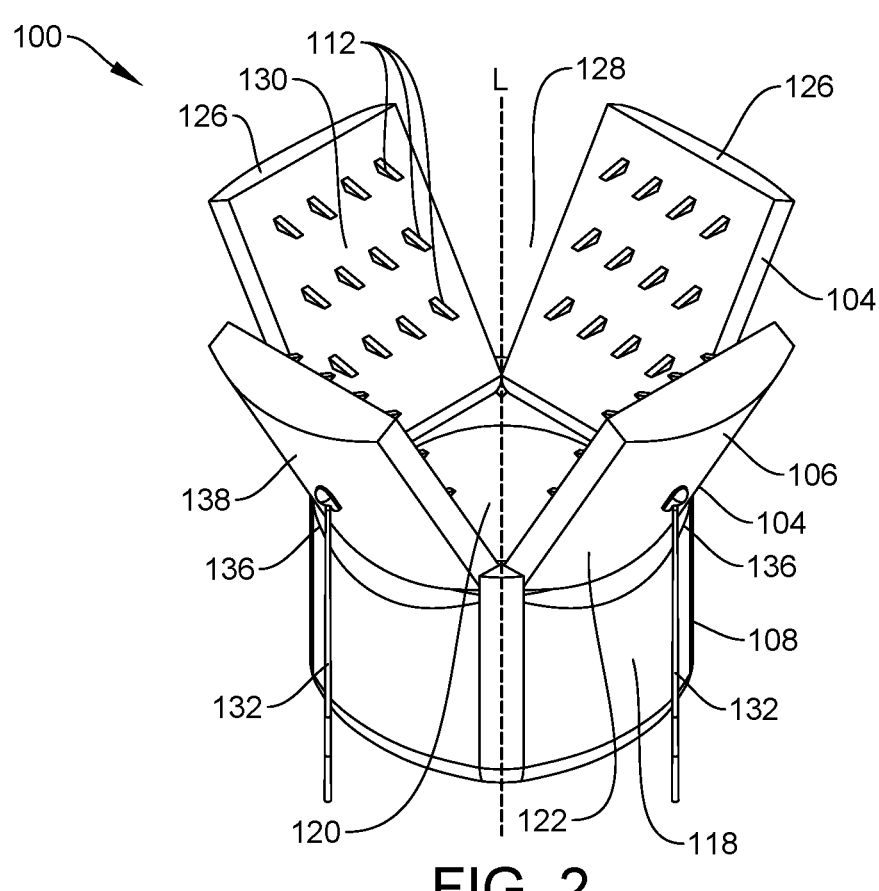
FIG. 2 shows a perspective view of the device according to FIG. 1, in a partially expanded configuration.
Figure 3:
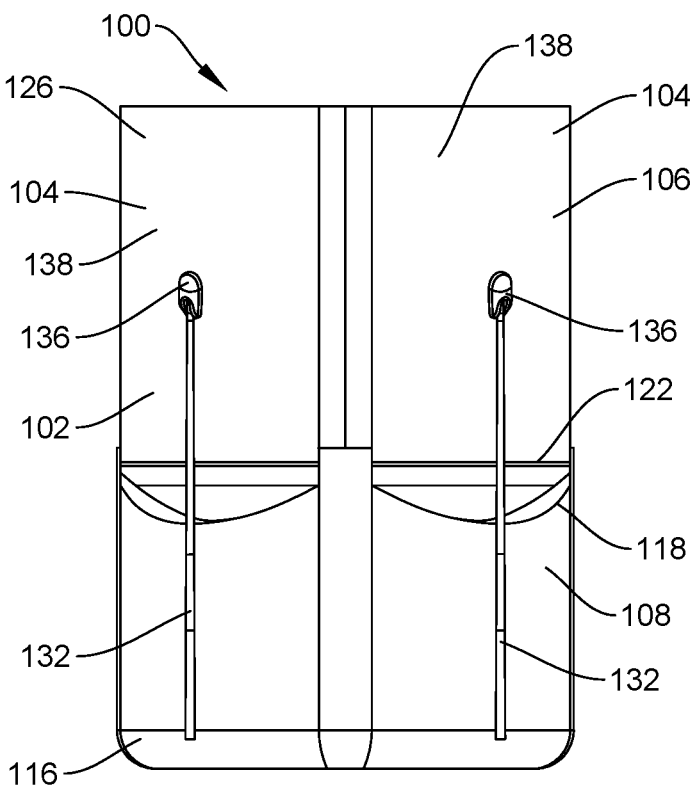
FIG. 3 shows a side view of the device according to FIG. 1, in the closed configuration.
Figure 4:
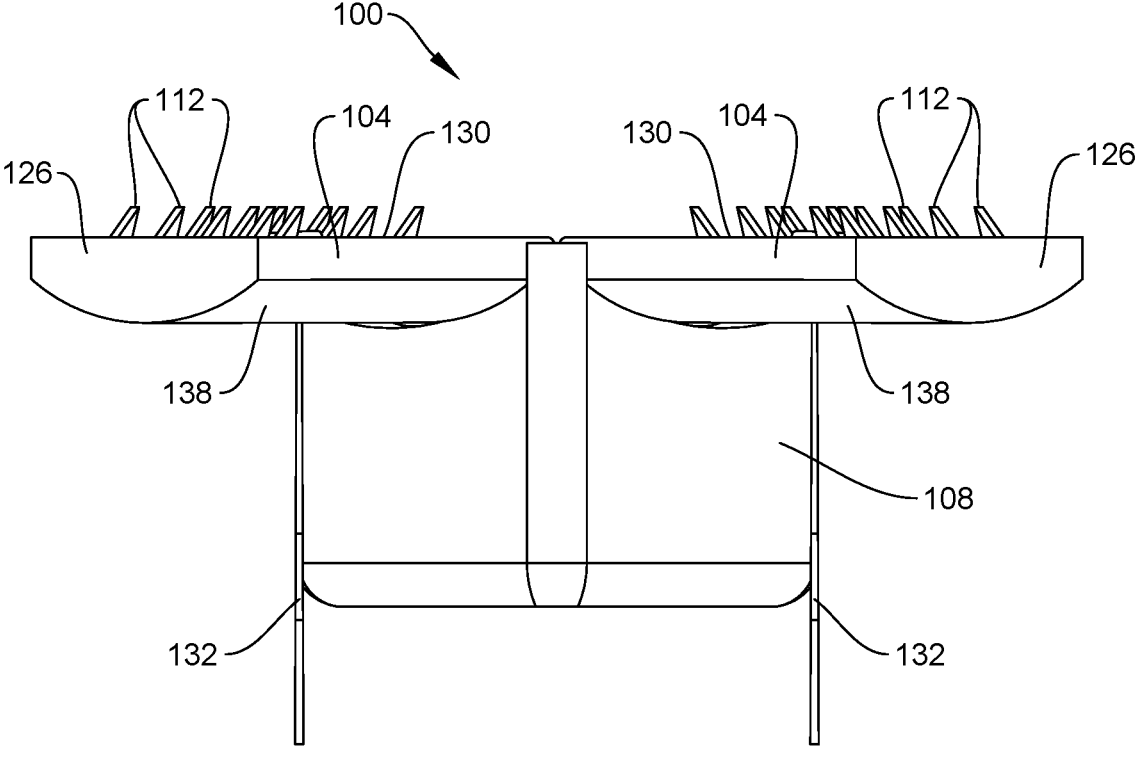
FIG. 4 shows a side view of the device according to FIG. 1, in the expanded configuration.

In an exemplary embodiment, the proximal portion 108 may include a plurality of protrusions 150 extending from the distal end 118. Each of the protrusions 150 include an opening 152 extending therein. Openings 152 of adjacent one of the protrusions 150 are aligned with one another and configured to receive, for example, a pin (not shown) configured to pivotally connect a corresponding one of the flaps 104 therebetween. According to an exemplary embodiment, each of the protrusions 150 may include two openings 152 so that each protrusion 150 facilitates a connection of two of the plurality of flaps 104 to the proximal portion 108. In an exemplary embodiment, the proximal portion 108 also includes a recess 154 along an exterior edge thereof, at the distal end 118, extending between each of the protrusions 150. Each recess 154 is sized shaped and configured to receive a portion of a corresponding one of the flaps 104 therein, when the flap is moved from the closed configuration toward the expanded configuration, as shown in FIGS. 2 and 4.

As described above, the distal portion 106 of the end cap 102 comprises the flaps 104 with each of the flaps 104 extending from a proximal end 122 pivotally connected to the distal end 118 of the proximal portion 108 to a distal end 126. According to an exemplary embodiment, as shown in FIG. 6, the proximal end 122 of each of the flaps 104 may include a hole 156 extending therethrough, the hole 156, sized shaped and configured to receive a pin therein for pivotally connecting the flap 104 to the proximal portion 108. For example, ends of the pin may extend from opposing ends of the hole 156 to be received within the openings 152 of adjacent ones of the protrusions 150 of the proximal portion 108. Thus, the flaps 104 may be pivoted relative to the proximal portion 108 between the closed configuration, in which the proximal and distal portions 108, 106 of the end cap 102 form a substantially continuous tube and the expanded configuration, in which the distal ends 126 of the flaps 104 are moved away from one another to expand a distal opening 128 of the end cap 102.

Although the exemplary embodiments show and describe a pivotal connection including for example, a pin, it will be understood by those of skill in the art that the flaps 104 may be coupled to the proximal portion 108 via any of a number of pivotal connections including, for example, via a living hinge or a spring.

In an exemplary embodiment, the flaps 104 are sized and shaped so that, in the closed configuration, the longitudinal edges 114 of each of the flaps 104 contacts a longitudinal edge 114 of an adjacent one of the flaps 104 so that, together, the flaps 104 form a substantially continuous tube that forms the distal portion 106 and which defines a channel 124. The channel 124 extends along the longitudinal axis L in alignment with the channel 120 so that, in the closed configuration, the entire end cap 102 (i.e., including the distal portion 106 and the proximal portion 108), forms a substantially continuous tube. In an exemplary embodiment, each of the flaps 104 extends substantially parallel to the longitudinal axis L. According to an exemplary embodiment, an exterior surface 138 of each of the flaps 104 is curved so that, in the closed configuration, the distal portion 106 is substantially cylindrical. It will be understood by those of skill in the art that this cylindrical shape may facilitate sliding of the clip along the distal portion 106.

As described above, the proximal end 122 of each of the plurality of flaps 104 is pivotally coupled to the distal end 118 of the proximal portion 108 so that the flaps 104 are movable between the closed configuration, described above, and the expanded configuration, in which each of the flaps 104 is pivoted relative to the proximal portion 108 so that distal ends 126 of the flaps 104 are moved away from one another and away from the longitudinal axis L. In an exemplary embodiment, the flaps 104 may pivot relative to the proximal portion 108 between an angle of approximately 0 degrees (closed configuration) and an angle of approximately 90 degrees (expanded configuration).

In one embodiment, in the expanded configuration, the flaps 104 may extend in a radially outward configuration, perpendicular relative to the longitudinal axis L. It will be understood by those of skill in the art, however, that the flaps 104 may extend at any of a variety of angles relative to the longitudinal axis L, in the expanded configuration. As the flaps 104 pivot from the closed configuration to the expanded configuration, the distal opening 128 via which tissue may be drawn into the channels 120, 124 of the end cap 102 is expanded. In particular, as will be described in further detail below, as the end cap 102 is moved from the expanded configuration to the closed configuration, tissue received between the flaps 104 will be drawn into the channel 124 formed thereby and/or into the channel 120 of the proximal portion 108.

In an exemplary embodiment, an interior surface 130 of each of the flaps 104 (i.e., a surface of the flap 104 which faces toward the longitudinal axis L, when the end cap 102 is in the closed configuration) may be substantially planar and includes a plurality of gripping features 112 configured to grasp tissue. Those skilled in the art will understand that the flaps 104 need not be planar and can be formed in any other desired shape so long as they combine to form a tissue receiving space of the desired dimensions. The gripping features 112 may include, for example, teeth or other protrusions which extend from the interior surface 130 to anchor the flaps 104 to the tissue and/or to grasp tissue over which the flap 104 is placed. Thus, as the end cap 102 is moved from the expanded configuration toward the closed configuration, tissue gripped via the gripping features 112 will be drawn into the channels 124, 120. The gripping features 112 may be particularly useful for treating tissue defects involving fibrotic or chronic tissue that is resistant to suction.

In an exemplary embodiment, the device 100 comprises a corresponding control member 132 coupled to each of the flaps 104 to move the flaps 104 between the closed and the expanded configurations. The control members 132 of this embodiment include, for example, a control wires, with each control wire extending between a distal end 134 connected to a corresponding one of the flaps 104 and a proximal end (not shown) accessible to a user (e.g., physician) at a proximal end of the scope device to which the end cap is coupled (e.g., with an actuator coupled to the proximal ends of the control members 132 at or adjacent to a handle of the scope device). Those skilled in the art will understand that the control members 132 may combine into or couple to a single control member at any point between the distal ends 134 and their proximal ends so that the control members may be operated in unison (to operate the flaps 104 in unison between the expanded and closed configurations) by moving the single control member proximally and distally (e.g., by operating an actuator to which the single control member is coupled).

The control members 132 may be moved longitudinally relative to the proximal portion 108 of the cap 102 (and the scope device) to correspondingly move the flaps 104. In particular, drawing the control members 132 proximally relative to the scope device (and the proximal portion 108 of the end cap 102) moves the flaps 104 from the closed configuration toward the expanded configuration, while moving the control members 132 distally relative to the scope device (and the proximal portion 108 of the end cap 102) moves the flaps 104 from the expanded configuration toward the closed configuration. Those skilled in the art will understand that the control members 132 are preferably formed to have a column strength sufficient to move the flaps 104 from the expanded to the closed configuration compressing the target tissue between the flaps 104. For example, the control members 132 may be formed of a relatively rigid materials such as PEEK tubing or any other suitably rigid biocompatible plastic tubing.

Figures 7, 8, 9:
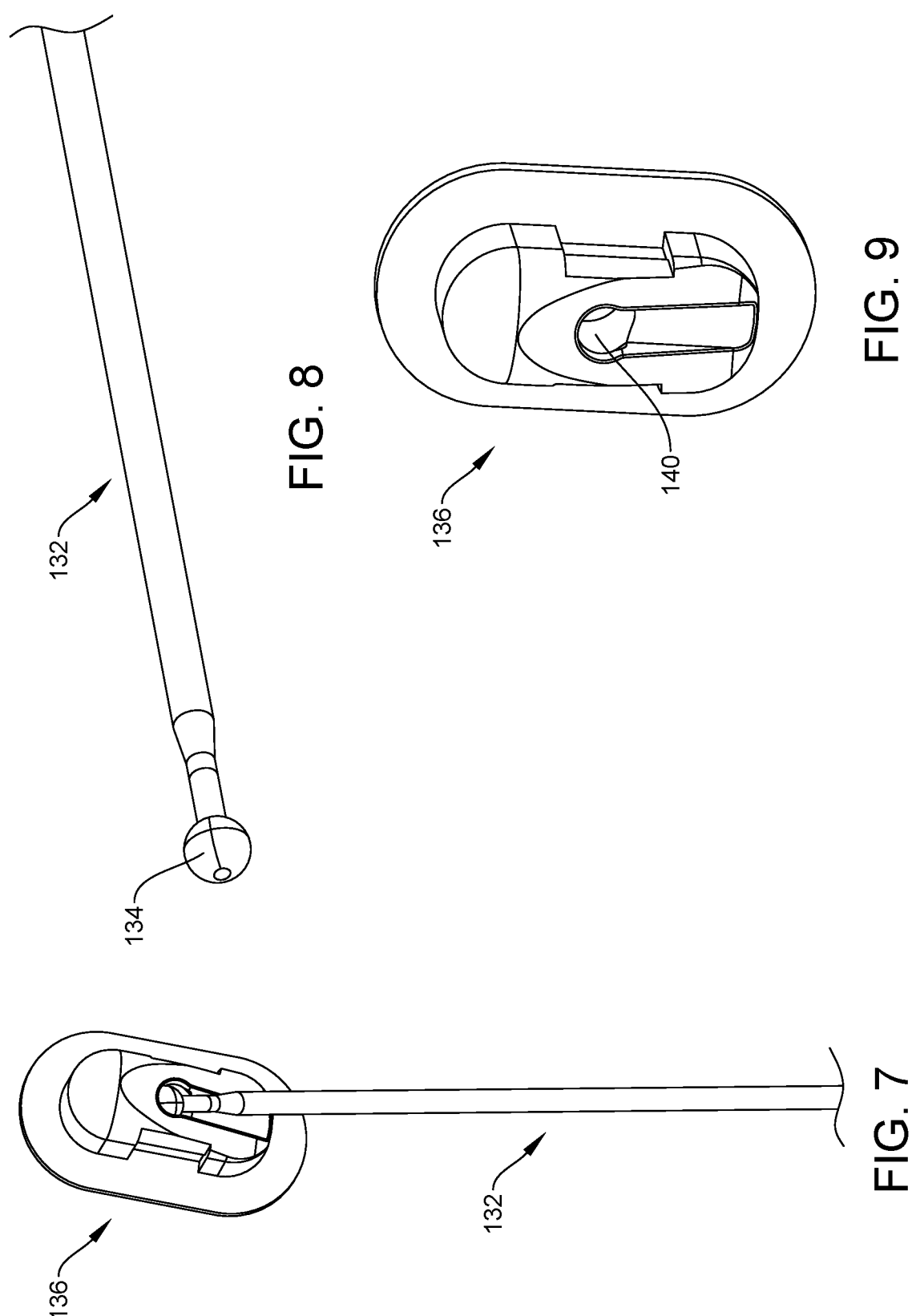
FIG. 7 shows a perspective view of a ball and yoke mechanism of the device according to FIG. 1.
FIG. 8 shows a perspective view of a control member of the device according to FIG. 1.
FIG. 9 shows a yoke component of the device according to FIG. 1.

In an exemplary embodiment, the control members 132 may be connected to the flaps 104 via a ball and yoke mechanism, as shown in FIG. 7. In this embodiment, the distal end 134 of each of the control members 132, as shown in FIG. 8, includes an enlarged ball that is sized, shaped, and configured to be movably received within a corresponding yoke component 136, which is attached to a surface of the corresponding flap 104. In an exemplary embodiment, as shown in FIG. 9, the yoke component 136 includes a socket 140 sized, shaped to correspond to the enlarged distal end 134 of the control member 132 so that, when the control members 132 are moved longitudinally relative to the scope device, the distal ends 134 rotate within the sockets 140 of the yoke components 136 as the flaps 104 pivot relative to the proximal portion 108 between the open and the expanded configurations.

In an exemplary embodiment, each of the flaps 104 includes the yoke component 136 along an exterior surface 138 thereof (i.e., a surface of the flap 104 facing away from the longitudinal axis L) so that each of the control members 132 extends along an exterior of the end cap 102 and the scope device to a proximal end of the scope device. Those skilled in the art will understand that any desired portion of the control members 132 may be housed in one or more tubes that may be clipped or otherwise removably fastened to an exterior of the scope device in any conventional manner to maintain control of the positioning of the control members 132 and/or to the prevent the movement of the control members 132 from irritating or being interfered with by contact with surrounding tissue.

According to an exemplary method utilizing the device 100, the end cap 102 is mounted over a distal end of a scope device oriented so that the control members 132 extend proximally along the scope device to a proximal end of the scope device. An over-the scope clip is positioned over the proximal portion 108 of the end cap 102 either prior to or after the cap 102 is mounted on the scope device and the scope device is then inserted to a target site within a patient's body via, for example, a body lumen accessed via a naturally occurring bodily orifice. The scope device is passed through the body lumen with the end cap 102 in the closed configuration, so that the proximal and distal portions 108, 106 together form a substantially tubular configuration to minimize any navigational issues and to minimize trauma to tissue along the path of the scope device.

Once at the target site, the end cap 102 is positioned adjacent target tissue to be treated and moved from the closed configuration to the expanded configuration by moving the control members 132 proximally with respect to the scope device (e.g., via manipulation of an actuator coupled to the control members 312). Drawing the control members 132 proximally relative to the scope device pivots the flaps 104 relative to the proximal portion 108 of the cap 102 so that the distal ends 126 of the flaps 104 move away from one another and away from the longitudinal axis L of the cap 102, expanding the distal opening 128 of the end cap 102 as described above.

Once the end cap 102 has been moved to the expanded configuration, negative pressure is applied through a working channel of the scope device to pass through the end cap 102. This suctions tissue adjacent to the distal opening of the cap 102 into the channel 120 of the cap 102. In addition, as tissue adjacent to the tissue that has been drawn into the channel 120 is pulled proximally into contact with the opened flaps 104, the gripping features 112 along the interior surfaces 130 of the flaps 104 penetrate and grip this surrounding tissue, so that, as the end cap 102 is moved from the expanded configuration to the closed configuration, this gripped tissue is drawn into the channel 124 defined via the gripping features 112 and the flaps 104 of the end cap 102.

As described above, the gripping features 112 in combination with the suction force (or a grasper or other tissue gripping device) applied through the end cap 102 may be particularly useful for treating fibrotic and/or chronic tissue that is resistant to suction and to increase the amount of tissue drawn into the cap 102 to increase the likelihood that a full-thickness portion of tissue or the full lateral extent of a target portion of tissue is clipped. It will be understood by those of skill in the art that the increased distal opening 128 formed via the flaps 104 in the expanded configuration allows a larger surface area of the target tissue to be eventually drawn within the channels 120, 124 so that, when the clip is deployed from the distal end of the cap 102, a larger portion of tissue is clipped.

After the end cap 102 has been moved to the closed configuration and the desired portion of target tissue is received in the channels 120, 124, the control members 132 are moved distally to move the over-the-scope clip distally along the end cap 102 until the clip moves off of the distal end of the cap 102 and snaps shut (e.g., under an inherent spring bias of the clip as would be understood by those skilled in the art) to clip the target tissue. As will be understood by those of skill in the art, the clip may be moved distally off of the end cap 102 toward a clipping configuration via any of a number of control mechanisms. In one embodiment as described above, the includes spring biased hinges connecting the jaws of the clip to bias the clip toward a clipping configuration in which the jaws are closed against one another.

The jaws of the clip are, when loaded onto the cap 102, spread open against this bias so that the jaws of the clip are primed to snap shut as soon as the clip is moved distally off the cap 102. By operating any known mechanism to move the clip distally off of the cap 102, the user can clip the clip over the tissue received within the cap 102. For example, in one embodiment, the clip may be releasably coupled to one or more control elements that pull the cap 102 proximally and prevent the clip from moving distally off of the cap 102. Then, when the user determines that the desired portion of tissue has been drawn into the cap 102, the user may release tension from these control elements permitting jaws of the clip to begin to close over a tapered surface of the cap 102 so that the bias of the hinges and the closing of the jaws pulls the clip distally off of the end cap 102 to clip the target tissue.

Once the clip has clipped the target tissue, the clip may be finally deployed by releasing the clip from the control elements. Although the clip is described as being permitted to slide distally off of the end cap 102, in another embodiment, control elements releasably coupled to the clip may be moved distally relative to the end cap 102 to push the clip off the end cap 102. It will be understood by those of skill in the art that although the exemplary embodiments show and describe the device 100 as being utilized with an over-the-scope clip, the end cap 102 of the device 100 may be used in conjunction with any of a variety of over-the-scope devices (e.g., bands) used to treat tissue defects in a similar manner.

Figure 10:
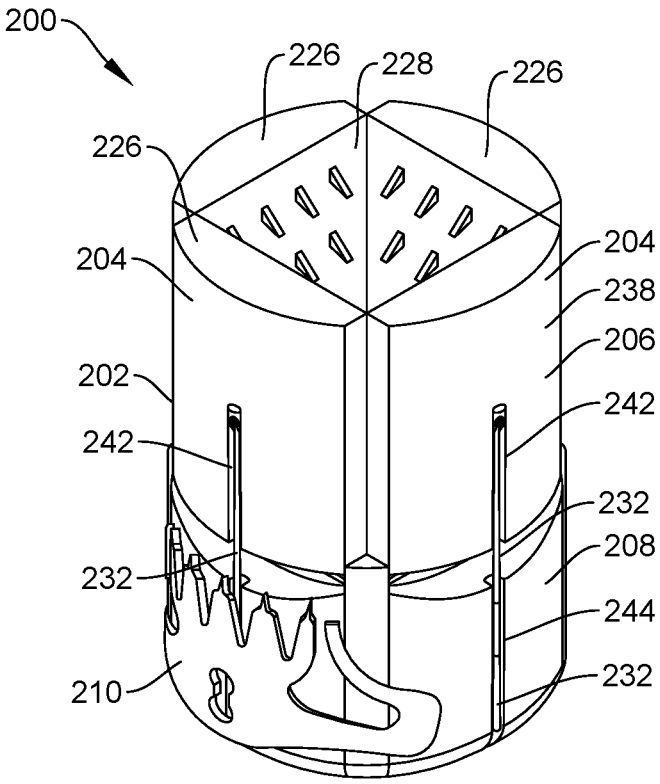
FIG. 10 shows a perspective view of a device according to another exemplary embodiment of the present disclosure.
Figure 11:
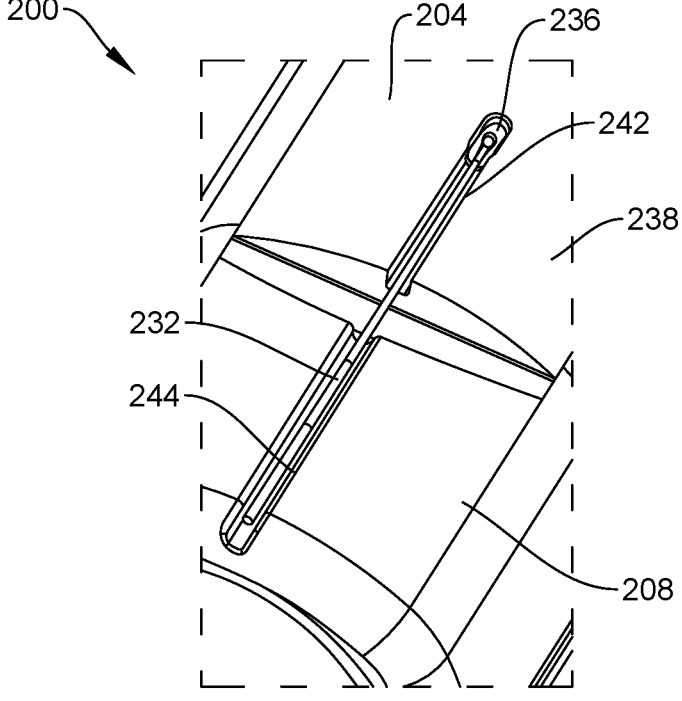
FIG. 11 shows an enlarged perspective view of a portion of the device of FIG. 8 including longitudinal grooves for receiving control members of the device therein.

As shown in FIGS. 10-11, a device 200 according to another exemplary embodiment of the present disclosure is substantially similar to the device 100, comprising an end cap 202 configured to be mounted over a distal end of a scope device for the application of, for example, an over-the-scope clip 210 over a target tissue. Similarly to the end cap 102, the end cap 202 of the device 200 includes a proximal portion 208 configured to accommodate the clip 210 thereover and a distal portion 206 including a plurality of flaps 204 pivotally coupled to the proximal portion 208. The flaps 204 are pivotable relative to the proximal portion 208 between a closed configuration, in which the flaps 204 are positioned relative to one another so that the end cap 202 (including the distal portion 206) forms a substantially tubular shape, and an expanded configuration, in which distal ends 226 of the flaps 204 are moved away from one another to expand a distal opening 228 of the end cap 202.

Similarly to the device 100, the device 200 includes control members 232 operable to move the flaps 204 between the closed configuration and the expanded configuration where each of the control members 232 is connected to a corresponding one of the flaps 204 via, for example, a ball and yoke mechanism. The end cap 202, however, further includes a longitudinal groove 242 extending along an exterior surface 238 of each of the flaps 204 (e.g., a surface of the flaps 204 facing away from a longitudinal axis along which the end cap 202 extends, when the end cap 202 is in the closed configuration) and a corresponding longitudinal groove 244 aligned with the longitudinal groove 242 along a portion of the proximal portion 208.

The longitudinal grooves 242, 244 extend along the flaps 204 and the proximal portion 208, respectively, to receive a yoke component 236 attached to the exterior surface 238 of a corresponding one of the flaps 204 and the control member 232 extending proximally therefrom. Thus, the yoke component 236 and the control member 232 reside within the longitudinal grooves 242, 244 so that they do not protrude beyond the exterior surface 238 surface of surrounding portions of the flaps 204 and an exterior surface of the proximal portion 208. Thus, the longitudinal grooves 242, 244 decrease the potential for interference between the control members 232 and the clip 210 as the clip 210 is slid along the end cap 202.

Figure 12:
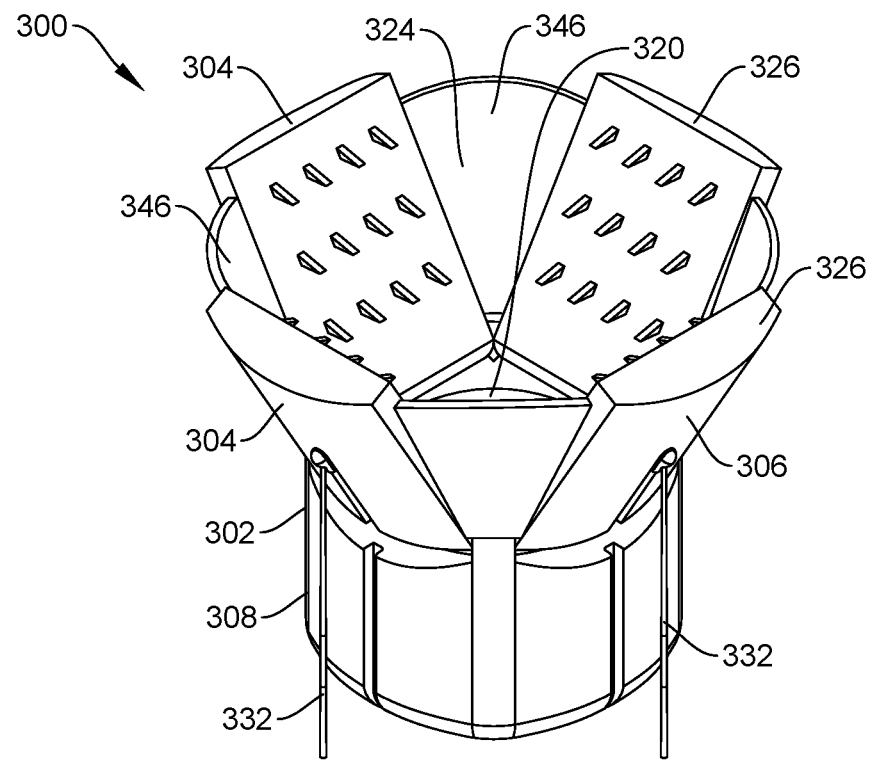
FIG. 12 shows a perspective view of a device according to another exemplary embodiment of the present disclosure.

As shown in FIG. 12, a device 300 according to a further exemplary embodiment of the present disclosure is substantially similar to the devices 100, 200 described above, comprising an end cap 302 and a plurality of control members 332 for moving the end cap 302 between a closed configuration and an expanded configuration. In particular, the end cap 302 includes a proximal portion 308 defining a channel 320 therethrough and a plurality of flaps 304 pivotally attached to the proximal portion 308 to define a distal portion 306. The flaps 304 are pivotable relative to the proximal portion 308 to move between a closed configuration, in which the flaps 304 are positioned such that the end cap 302 forms a substantially tubular shape, and an expanded configuration, in which distal ends 326 of the flaps 304 are moved away from one another.

The end cap 302, however, further comprises a plurality of flexible membranes 346, with each of the flexible membranes 346 extending between and connecting adjacent ones of the plurality of flaps 304. When the end cap 302 is in the closed configuration, the flexible membranes 346 may fold onto itself, permitting the flaps 304 to be drawn toward one another. When the end cap 302 is in the expanded configuration, however, the flexible membranes 346 may unfold and/or stretch to form a webbing between the adjacent flaps 304. The flexible membranes 346 may be formed of any of a variety of materials such as, for example, silicone, a PET thermoplastic, or any material having a durometer which permits flexure and/or stretch. Those skilled in the art will understand that the flexible membranes 346 may be configured to bias the flaps 304 toward the closed configuration to help in moving the flaps 304 to the closed configuration against the resistance imparted by tissue drawn into the end cap 302. Alternatively, a circular ring of flexible material be substituted for the flexible membranes 346 if it were desired to achieve this bias toward the closed configuration without sealing the spaces between the flaps 304.

In this embodiment, the flexible membranes 346 connect adjacent ones of the flaps 304 so that the flaps 304 and the flexible membranes 346 together define a channel 324 extending through the distal portion 306 of the end cap 302 and so that spaces between the flaps 304 are substantially sealed preventing tissue from becoming lodged between flaps 304 and facilitating the movement of the flaps 304 to the closed configuration. In the expanded configuration, a cross-sectional area of the channel 324 extending through the distal portion 306 increases to permit larger surface area of target tissue to be received therein.

Figure 13:
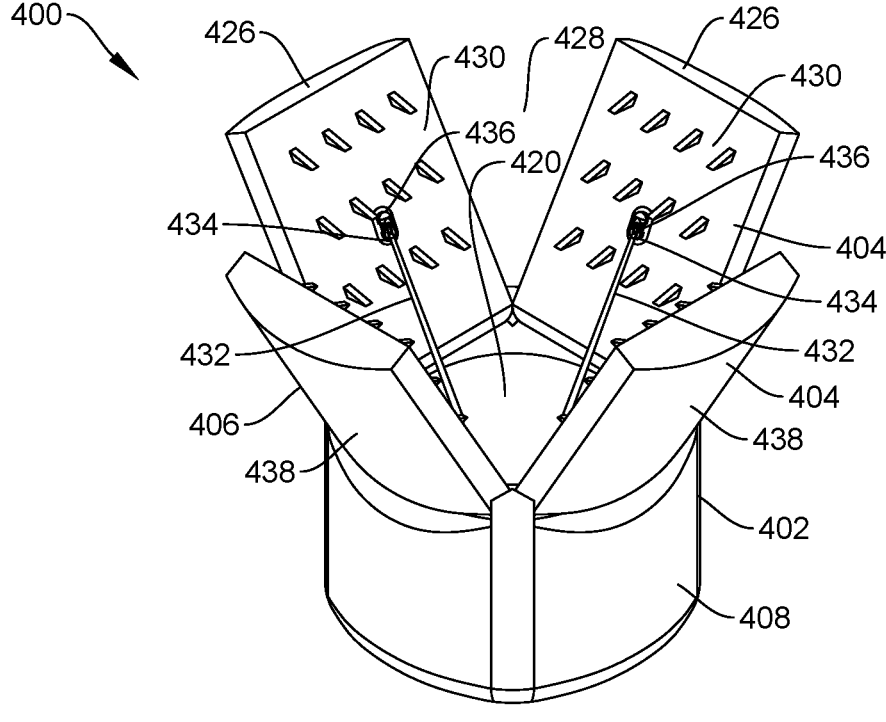
FIG. 13 shows a perspective view of a device according to yet another exemplary embodiment of the present disclosure.

As shown in FIG. 13, a device 400 according to yet another exemplary embodiment of the present disclosure is substantially similar to the device 100, comprising an end cap 402 including a proximal portion 408 and a plurality of flaps 404 pivotally connected to the proximal portion 408 to define a distal portion 406 movable between a closed configuration, in which the flaps 404 contact one another to form a substantially tubular shape, and expanded configuration, in which distal ends 426 are moved away from one another to increase a distal opening 428 of a channel 420 of the end cap 402. Similarly to the end cap 102, the flaps 404 of the end cap 402 are moved between the closed and the expanded configurations via control members 432 connected to the flaps 404. Rather than being connected to an exterior surface 438 of the flaps 404, however, a distal end 434 of each of the control members 432 is connected to an interior surface 430 of a corresponding one of the flaps 404.

Similarly to the device 100, the distal end 434 of the control member 432 of this embodiment includes, for example, an enlarged ball movably received within a yoke component 436 having a correspondingly shaped socket 440, the yoke component 436 being connected to the interior surface 430 of the flap 404. Since the control members 432 are connected to the interior surfaces 430 of the flaps 404, however, it will be understood by those of skill in the art that the control members 432 will extend proximally from the yoke components 436, through the channel 420 of the end cap 402 and through a channel of the scope device to a proximal end thereof thereby eliminating any contact between the control members 432 and the yoke components 436 and surrounding tissue during insertion and withdrawal of the scope device to the target site within the body.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

What is claimed is:

1. A device for facilitating an over-the-scope application of a tissue treating element, comprising: an end cap including a proximal portion configured to be mounted over a distal end of a scope device and a distal portion extending distally therefrom, the proximal portion extending along a longitudinal axis from a proximal end to a distal end and including a proximal channel extending therethrough, the distal portion including a plurality of flaps, a proximal end of each of the flaps pivotally connected to the distal end of the proximal portion so that the flaps are movable between a closed configuration, in which the flaps define a distal channel in alignment with the proximal channel, and an expanded configuration, in which distal ends of the flaps are moved away from one another to expand a distal opening of the end cap; and a plurality of control members, a distal end of each of the control members connected to a corresponding one of the flaps so that a longitudinal movement of the control members relative to the proximal portion of the end cap moves the flaps relative to the proximal portion between the closed configuration and the expanded configuration, wherein the distal end of each of the control members includes an enlarged ball received within a correspondingly shaped socket of a yoke component that is connected to the corresponding one of the plurality of flaps.

2. The device of claim 1, wherein an interior surface of the plurality of flaps includes a plurality of gripping features configured to anchor the flaps to s target tissue.

3. The device of claim 2, wherein the plurality of gripping features includes teeth protruding from the interior surface of the plurality of flaps.

4. The device of claim 1, wherein an exterior surface of each of the plurality of flaps are curved to facilitate a sliding of a tissue clipping device therealong.

5. The device of claim 1, wherein, in the closed configuration, each of the flaps extend substantially parallel relative to the longitudinal axis and a longitudinal edge of each of the flaps contacts a longitudinal edge of an adjacent one of the flaps to define the distal channel therebetween.

6. The device of claim 1, wherein the distal end of each of the control members are connected to an exterior surface of the corresponding one of the flaps so that the control members extend along an exterior of the end cap.

7. The device of claim 1, wherein the distal end of each of the control members are connected to an interior surface of each of the corresponding one of the flaps so that the control members extend proximally therefrom through the proximal channel of the end cap.

8. The device of claim 1, wherein the ball rotatable within the socket as the end cap is moved between the closed configuration and the expanded configuration.

9. The device of claim 1, wherein each of the plurality of flaps includes a longitudinal groove extending therealong and the proximal portion includes a corresponding groove therealong in longitudinal alignment with the longitudinal groove, the longitudinal groove and the corresponding groove configured to receive the control member therein.

10. The device of claim 1, wherein the end cap further includes a flexible membrane extending between adjacent ones of the plurality of flaps so that, in the expanded configuration, the flexible membrane stretches to increase a cross-sectional area of the distal channel.

11. The device of claim 10, wherein the flexible membrane is formed of a material including one of silicone and PET thermoplastic.

12. An end cap configured to be mounted over a distal end of a scope to facilitate to facilitate an over-the-scope application of a tissue gripping device, comprising: a proximal portion extending along a longitudinal axis from a proximal end to a distal end and including a proximal channel extending therethrough; and a distal portion including a plurality of flaps, a proximal end of each of the flaps pivotally connected to the distal end of the proximal portion so that the flaps are movable between a closed configuration, in which the flaps define a distal channel in alignment with the proximal channel, and an expanded configuration, in which distal ends of the flaps are moved away from one another, wherein the plurality of flaps is configured to be moved between the closed configuration and the expanded configuration via a plurality of control members, a distal end of each of the control members including a ball received within a correspondingly shaped socket of a yoke component that is connected to the corresponding one of the plurality of flaps.

13. The end cap of claim 12, wherein an interior surface of the plurality of flaps includes a plurality of gripping features configured to anchor the flaps to a target tissue.

14. The end cap of claim 12, wherein, in the closed configuration, each of the flaps extend substantially parallel relative to the longitudinal axis and a longitudinal edge of each of the flaps contacts a longitudinal edge of an adjacent one of the flaps to define the distal channel therebetween.

15. The end cap of claim 12, further comprising a flexible membrane extending between adjacent ones of the plurality of flaps so that, in the expanded configuration, the flexible membrane stretches to increase a cross-sectional area of the distal channel.

16. A method for treating tissue, comprising: mounting an end cap over a distal end of a scope device and inserting the distal end of the scope device, with the end cap in a closed configuration, to a target area within a body lumen to be treated, the end cap including a proximal portion defining a proximal channel therein and a distal portion including a plurality of flaps, a proximal end of each of the flaps pivotally coupled to the proximal portion, the plurality of flaps contacting one another to define a distal channel therebetween, in the closed configuration; moving the end cap from the closed configuration toward an expanded configuration by pivoting the flaps relative to the proximal portion so that distal ends of the flaps are moved away from one another to expand a distal opening of the proximal channel, the end cap movable between the closed configuration and the expanded configuration by moving a plurality of control members relative to the scope device, a distal end of each of the control members including a ball received within a correspondingly shaped socket of a yoke component that is connected to the corresponding one of the plurality of flaps; moving the end cap from the expanded configuration toward the closed configuration, via the control members and sliding an over-the-scope clip, positioned over the proximal portion of the end cap, distally off of the end cap.

17. The method of claim 16, further comprising pressing tissue gripping features along an interior surface of the plurality of flaps along the target tissue to anchor the flaps to the target tissue so that moving the end cap from the expanded configuration toward the closed configuration draws the target tissue into the distal channel formed via the plurality of flaps.

18. The method of claim 16, wherein the flaps are moved between the closed configuration and the expanded configuration via the control members, a distal end of each of the control members connected to a corresponding one of the flaps so that a longitudinal movement of the control members relative to the proximal portion of the end cap and the scope device correspondingly moves the flaps between the closed configuration and the expanded configuration.

19. The method of claim 16, wherein, in the closed configuration, each of the flaps extends substantially parallel relative to a longitudinal axis so that the end cap extends along a substantially cylindrical shape.

* * * * *